US00PP10412P

United States Patent [19]

Swartz et al.

[11] Patent Number: Plant 10,412

[45] Date of Patent: May 26, 1998

[54] RASPBERRY PLANT NAMED 'CAROLINE'

[76] Inventors: Harry Jan Swartz, 16022 Jerald Rd., Laurel, Md. 20707; Joseph A. Fiola, 1400 Paterson Ave., Whiting, N.J. 08759; Herbert D. Stiles, 811 Brunswick Ave., Blackstone, Va. 23824; Brian A. Smith, 311 N. Dallas St., River Falls, Wis. 54022

[21] Appl. No.: 630,181

[22] Filed: Apr. 10, 1996

[51] Int. Cl.[6] ..... A01H 5/00

[52] U.S. Cl. ..... Plt./46.2

[58] Field of Search ..... Plt./46.2

[56] References Cited

U.S. PATENT DOCUMENTS

P.P. 6,493 12/1988 Wilhelm ..... Plt./46.2

*Primary Examiner*—James R. Feyrer

*Attorney, Agent, or Firm*—Marian P. Marks; Sana A. Pratt

[57] ABSTRACT

This invention relates to a new and distinct fall bearing red raspberry cultivar named 'Caroline' which is capable of producing a large amount of larger, more flavorful and more cohesive fruit on primocanes 1–3 weeks earlier than standard cultivars. The cultivar is characterized by its moderate to high suckering ability, its conic, smooth and symmetrical fruit. Additionally, its thorn characteristics and its upright canes with fall fruit appearing on the upper half of the cane.

4 Drawing Sheets

ORIGIN OF THE NEW CULTIVAR

The new cultivar of fall bearing red raspberry originated from a controlled cross at the University of Maryland Greenhouses in College Park, Md. The cross, "CR", was 'GEO-1'×'Heritage' and was made in winter of 1989. 'GEO-1' was a seedling from the cross 'Autumn Bliss'× 'Glen Moy'. This year was designated "J", as part of the University of Maryland at College Park; Rutgers University of New Brunswick, N.J; Virginia Polytechnic Institute and State University, Southern Piedmont Agricultural Research and Education Center at Blackstone; and the University of Wisconsin at River Falls cooperative breeding program. The clone was the first of the progeny selected in 1991 at the Rutgers site near Cream Ridge, N.J. and was therefore designated "-f1". Thus the complete breeding designation was "JCR-f1".

The new cultivar has been reproduced asexually by tissue culture techniques at Nourseberry Farm, 41 River Road, South Deerfield, Massachusettes 01373, and tested in evaluation fields first by the cooperating breeders, and then by licensed evaluators. Through the several thousand plants produced by tissue culture and standard asexually reproduced plants from root suckers, no off-type phenotype plants have been noted.

The seedling clone "JCF-f1" has been designated cultivar 'Caroline' upon agreement of all cooperators and representatives.

SUMMARY OF THE NEW CULTIVAR

This application relates to a new and distinct everbearing red raspberry culivar, botanically known as *Rubus ideaus* L.. The following characteristics are outstanding:

1. Production of large quantities of fruit on floricanes 1 to 3 weeks earlier than the standard cultivars currently in widespread use.

2. In warmer climates, fruit is larger, more flavorful and more cohesive (does not crumble) than currently used fall bearing cultivars.

The following characteristics are distinguishing and can be useful for cultivar identification.

1. Plants are moderately suckering, upright, producing around to 75% as many canes as 'Heritage', one of its parents.

2. Fruit is conic, smooth and symmetrical, with a slightly greater length to width ratio than 'Heritage'.

4. Fruit has an even collar.

5. Plants are distinguishable from 'Heritage' by thorn and leaf shape and coloration.

BRIEF DESCRIPTION OF THE PHOTOGRAPHS

The accompanying photographs show typical characteristics of the new variety:

Figure 4:
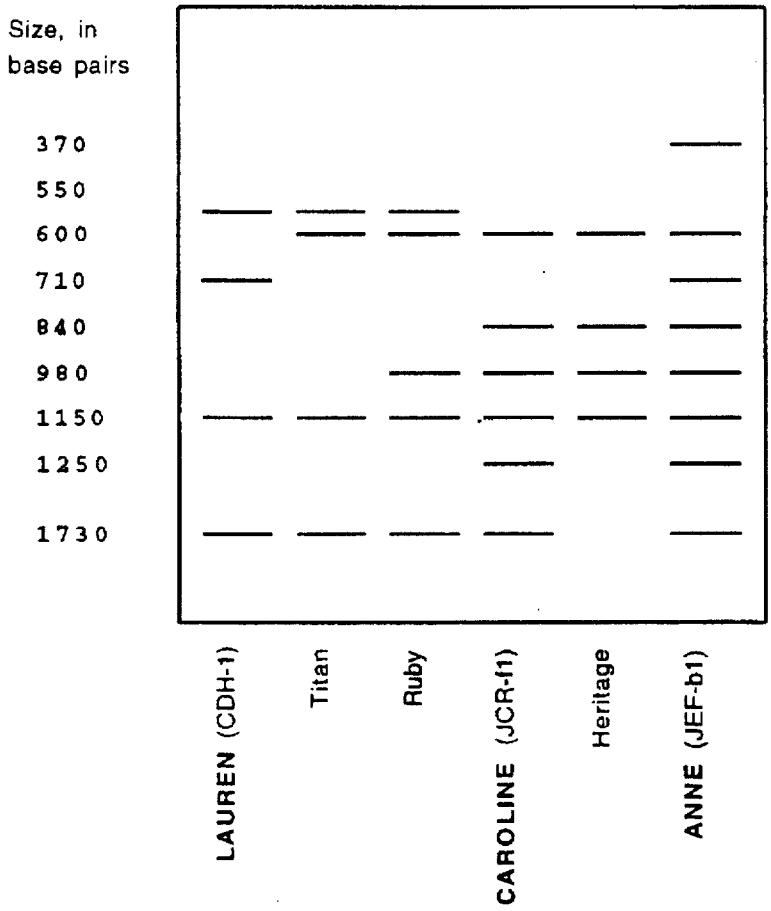

The FIG. 4 depicts the DNA fingerprints of JCR-f1, 'Heritage', 'Ruby'—another 'Heritage' cross— and several other raspberry cultivars.

DESCRIPTION OF THE NEW CULTIVAR

The following is a detailed description of the new cultivar, including fruit production, together with the cultivar's morphological characteristics. The characteristics of the cultivar are compared to the standard used in the area: 'Heritage'. This description is based on information provided by cooperating scientists from plants grown in fields at Queenstown, Md., Cream Ridge, N.J., Blackstone, Va. and River Falls, Wis. Rock Hall, Pa., and from plants grow in the greenhouse at College Park.

Fruit Production

JCR-f1 has been tested in a replicated planting in Queenstown, Md., Rock Hall, Pa. and Cream Ridge, N.J.. The following data were taken in each location in the summers of 1994 and 1995. Early yield is fruit picked before Sep. 1, 1994.

TABLE 1

Comparison of fresh fruit characteristics of Heritage and JCR-f1

| | | JCR-f1 | Heritage |
|---|---|---|---|
| Yield in thousands of lbs/acre | NJ, 1994 | 7.1 | 4.9 |
| | NJ, 1995 | 7.8 | 8.1 |
| | MD, 1994 | 6.2 | 7.3 |
| | PA, 1995 | 3.0 | 1.4 |
| Fruit Weight in grams/fruit | NJ, 1994 | 2.0 | 1.7 |
| | NJ, 1995 | 1.9 | 1.7 |
| | MD, 1994 | 1.8 | 1.4 |
| | PA, 1995 | 2.5–1.9 | 1.9–1.4 |
| Early Yield (thousand lbs/acre) | NJ | 1.6 | 0.1 |
| | MD | 4.6 | 3.1 |
| Fruit Width (cm) | | 1.86 | 1.4 |
| Fruit Length (cm) | | 1.75 | 1.55 |
| Cavity diameter (cm) | | 0.76 | 0.77 |
| Seed weight (mg) | | 1.40 | 1.16 |

In 1994, 30% of the 'Heritage' produced in Maryland showed infection by late yellow rust, whereas only 3% of JCR-f1 showed infection by rust.

Plant Characteristics

Figure 1:
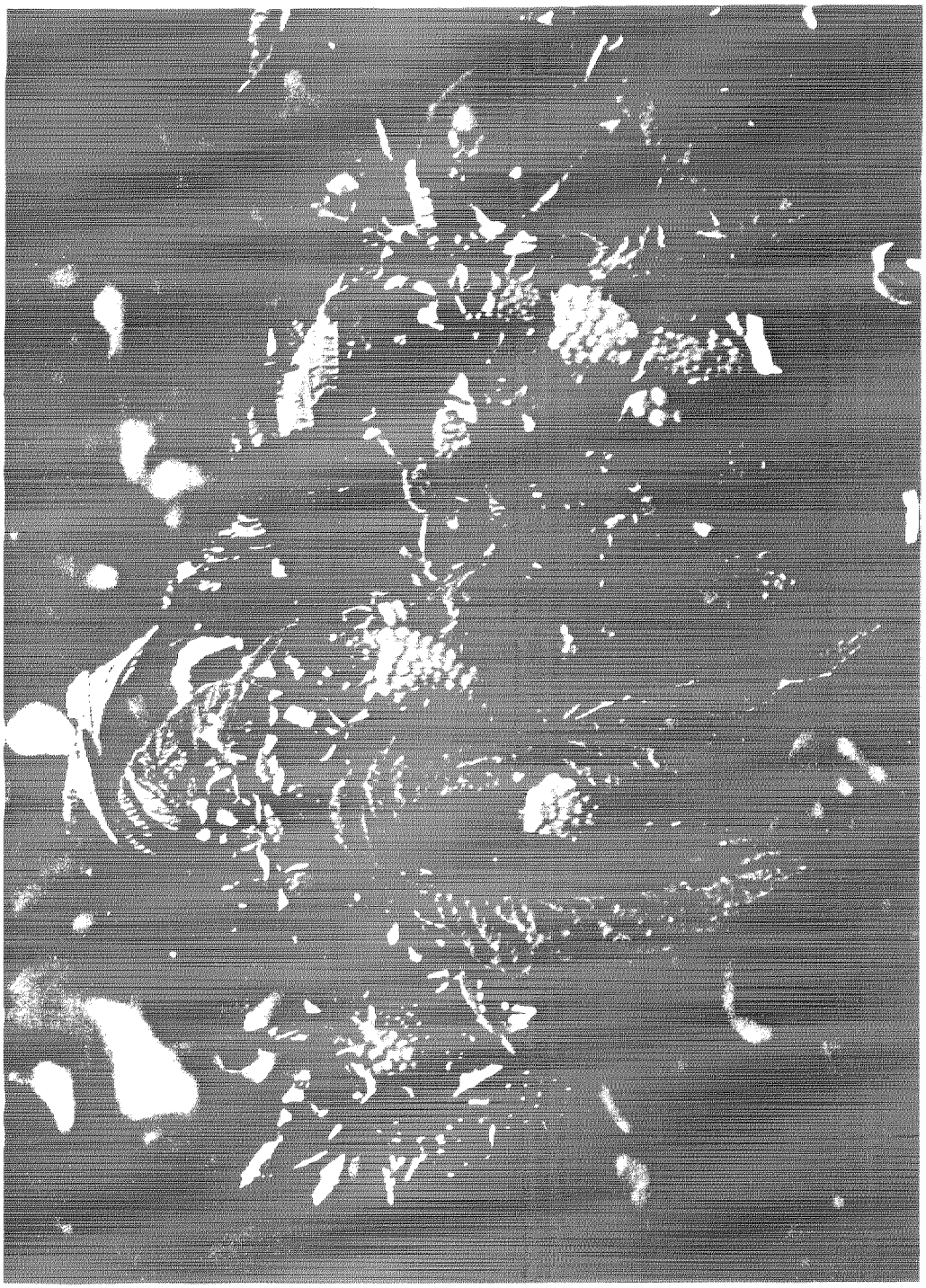
FIG. 1 shows a fruiting cluster of JCR-f1, showing the exposure of the fruit.
Figure 2:
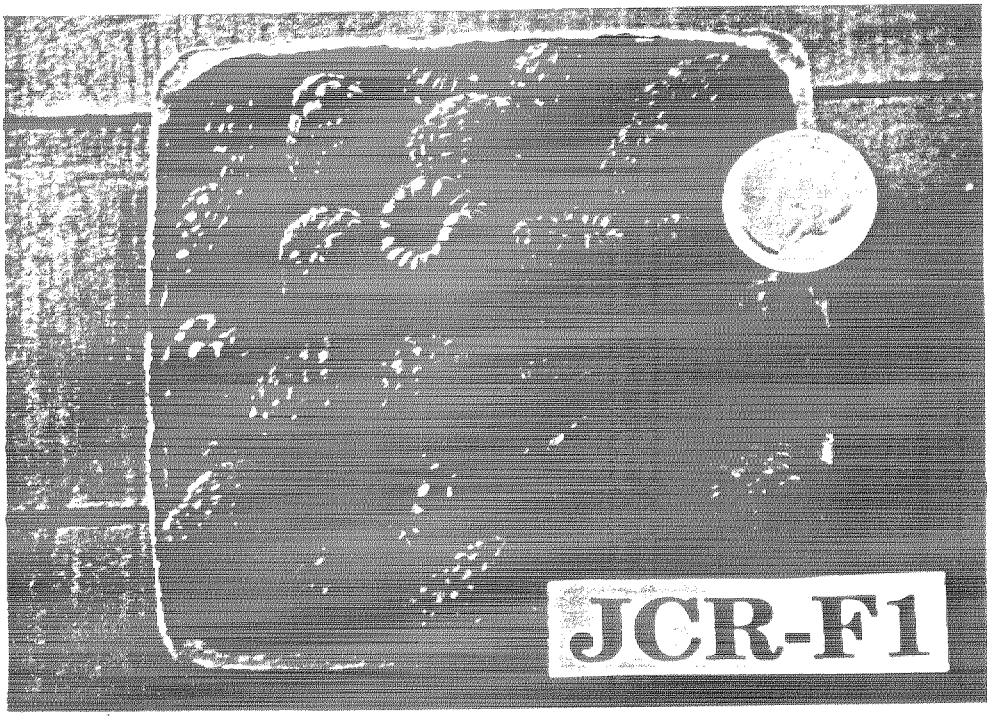
FIG. 2 shows the harvested fruit of JCF-f1.
Figure 3:
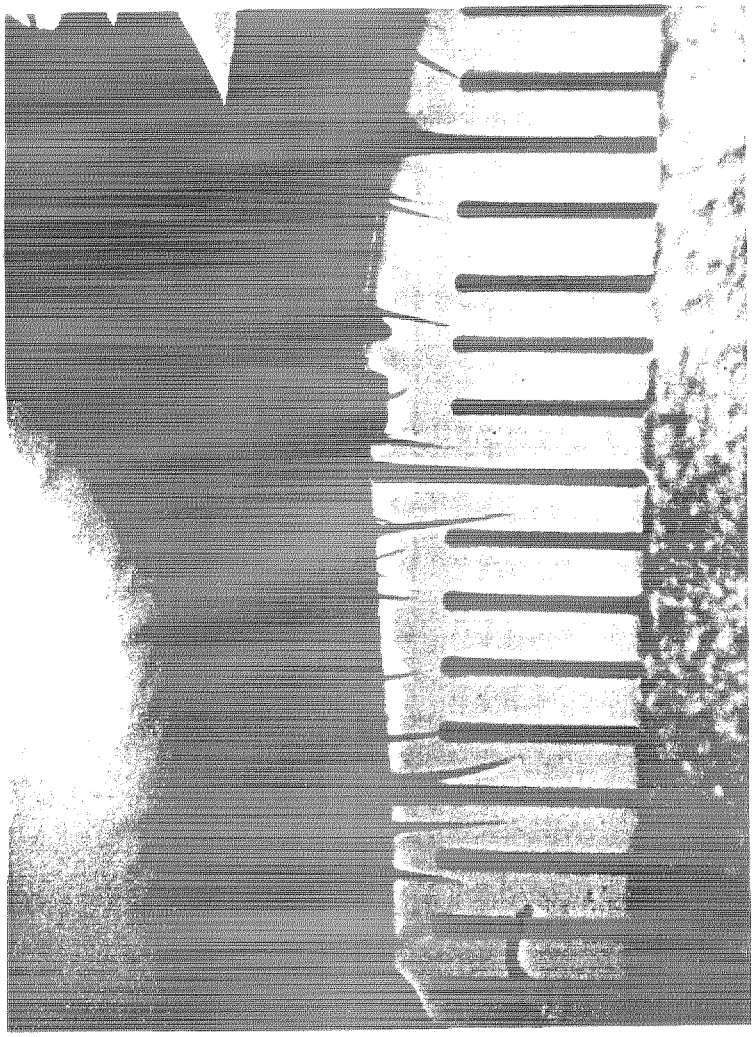
FIG. 3 shows the prickles of JCR-f1.

JCR-f1 produces a moderate to high number of upright root suckers. During the growing season, canes are green with large areas of red. The erect canes will branch occasionally and are moderately vigorous depending on location. Thorns are numerous (20–50 per node on vigorous canes, more on non-vigorous canes), thinner than 'Heritage', 1–4 mm in length and dark brown (see FIG. 3). Leaves are of Royal Horticultural Society (R.H.S.) color chart number 137A, large and commonly trifoliate, pentafoliolate on vigorous primocanes. Young leaf color is slightly darker than that of young 'Heritage' leaves, and without the red coloration often observed on expanding 'Heritage' leaves. Serration is similar to other 'Heritage' types. Fall fruit is borne on the top half to one third of the primocane or, in the lower half of the cane early in the summer floricane season. Fruit trusses are cymose clusters. Flowers are perfect and indistinguishable from other raspberry cultivars. Fruit are red, firm, symmetrical, readily separated from the torus, truncated conic, and more cohesive than fruit of 'Heritage'. Fruit has R.H.S. color chart number 45A, is sweet to tart in flavor, more reminiscent of 'Glen Moy' than 'Heritage'. The plant is field tolerant to several diseases including: mildew, anthracnose, and verticillium wilt. JCR-f1 leaves will develop late season rust, however, its fruit is less susceptible than fruit of 'Heritage' to rust.

Plant attitude at maturity is upright to slightly arching, requiring support with a full crop. Plants should be trellised on a simple 2 foot horizontal wire "containment" trellis typical of fall bearers. Pruning and training is typical for a fall bearing cultivar, i.e. February to March mowing to 4–6 inches in height. Bark is green through the season, turning brown in fall and exfoliating thereafter. Flowers are indistinguishable from other raspberry cultivars. Plants are self pollinating. Internode length is highly dependent on light and time of year; in the shade, lengths can exceed 2 inches, while in the late fall and in full sun, lengths are often less than one half inch. Cane density is high, requiring mowing or tilling to reduce the size of the row. This results in a dense leaf canopy. Fruit are easily removed from the plant. The fruit are only moderately firm in warm weather. No mechanical harvesting tests have been performed.

Leaflets range from 3–8 inches from base of petiole to apex of terminal leaflet blade. Primocane leaflet length is 8–22 cm. Terminal leaflet blade is 13.8 cm in length by 10.6 cm in width. Petiole length is 7.8 cm. Petiole diameter is 3.6 mm.

The measured weight of fruit in New Jersey in 1994 varied through the season and was measured from yields in August at 2.4 grams/berry, decreasing in size through the season reaching a size of 1.5 grams/berry in October, with an average weight of 1.8 grams/berry for the season. The measured weight of fruit in Maryland in 1994 varied through the season and was measured from yields in July at 2.2 grams/berry, decreasing in size through the season reaching a minimum in size of 1.5 grams/berry in mid-August, and increasing in weight to 1.9 grams/berry by mid-September. The average weight of fruit for the season was 1.9 grams/berry.

Nucleic Acid Fingerprinting

The unique DNA fingerprint of JCR-f1 was produced by random amplified polymorphic DNA (RAPD) analysis. Leaf DNA's were isolated using a modified CTAB( hexadecyl trimethyl ammonium bromide) procedure (Rowland and Nguyen, 1993, *Biotechniques* 14: 735–736) without the final PEG precipitation step.

Amplification reactions were performed in volumes of 25 μl using a procedure described in Levi et. al., 1993, HortScience 28: 1188–1190). The reagents and conditions included 50 mM Tris HCL-pH 9.0, 20 mM NaCl, 4 mM $MgCl_2$, 1% Triton X-100, 0.1% Gelatin, 0.2 μM primer (Promega 80-34), 200 μM of each dNTPs, 0.028 units/μl of Taq DNA polymerase (Promega Corporation, Madison, Wis.) and 1 mg/ml of template DNA. The oligonucleotide primer was synthesized by Promega Inc., Madison, Wis.

DNA was amplified in a MJ programmable thermal control (Model PTC-100, MJ Research, Watertown, Mass.) programmed for 51 cycles of 40 sec at 94° C., 70 sec at 48° C., and 2 min at 72° C. Amplification products were analyzed by electrophoresis at 90 constant voltages in 1.4% Sigma agarose gels with 0.5×TBE buffer. DNA bands were detected under UV light after staining with ethidium bromide and visualized by producing a negative image on a computer. Comparison of bands with a 123 base pair ladder indicate the presence of JCR-f1 bands at 600, 840, 980, 1150, 1250, and 1730 bp; 'Ruby' bands at 550, 600, 980, 1150, and 1730 bp; and 'Heritage' bands at 600, 840, 980, and 1150 bp.in primer 80-34. The existence of bands unique to JCR-f1 under the conditions of this test is proof of fundamental genetic differences between JCR-f1 and 'Ruby' and 'Heritage', the only other high yielding, fall bearing, red-fruited cultivar in the eastern U.S.

What is claimed is:

1. A new and distinct fall bearing red raspberry plant known as 'Caroline' as described herein, illustrated and identified by the characteristics set forth above.

* * * * *

PLT-204 SR
C5203 OR PP 010,412

*Fig.* 1

DNA Bands for 'Lauren', 'Titan', 'Ruby', 'Caroline', 'Heritage', and 'Anne'